United States Patent [19]

Feldman et al.

[11] 3,999,546
[45] Dec. 28, 1976

[54] DIAPER HAVING PRIMARY AND SECONDARY TAB FASTENERS

[75] Inventors: Mark I. Feldman, Chicago; Ludwig Tritsch, Wilmette, both of Ill.

[73] Assignee: Johnson & Johnson, New Brunswick, N.J.

[22] Filed: Dec. 19, 1975

[21] Appl. No.: 642,431

[52] U.S. Cl. .............................. 128/284; 128/287
[51] Int. Cl.² ........................................ A61F 13/16
[58] Field of Search .................... 128/284, 287; 24/DIG. 11, 73 VA

[56] References Cited
UNITED STATES PATENTS

| | | | |
|---|---|---|---|
| 3,848,596 | 11/1974 | Pennau | 128/284 |
| 3,869,761 | 3/1975 | Schaar | 128/284 X |
| 3,930,502 | 1/1976 | Tritsch | 128/287 |
| 3,951,149 | 4/1976 | Ness | 128/287 |

*Primary Examiner*—Aldrich F. Medbery

[57] ABSTRACT

A disposable diaper having a facing sheet defining a diaper inside surface and a backing sheet defining a diaper outside surface is provided with adhesive tabs comprising a backing web, a first tape segment and a second tape segment. The backing web is folded over to form a pair of anchoring legs which are permanently attached to a marginal portion of the diaper received therebetween. First and second tape segments each have a fixed end attached to the same anchoring leg, and a free end which is folded about the edge of the diaper and releasably attached to an underlying release means. The free end of the first tape segment is separable from a first release means carried on the free end of the second tape segment to make the first tape segment available for use in securing the diaper about an infant. The first tape segment can be severed to remove the diaper from the infant, and the free end of the second tape segment can be separated from a second release means carried on the other anchoring leg to refasten the diaper about an infant.

14 Claims, 5 Drawing Figures

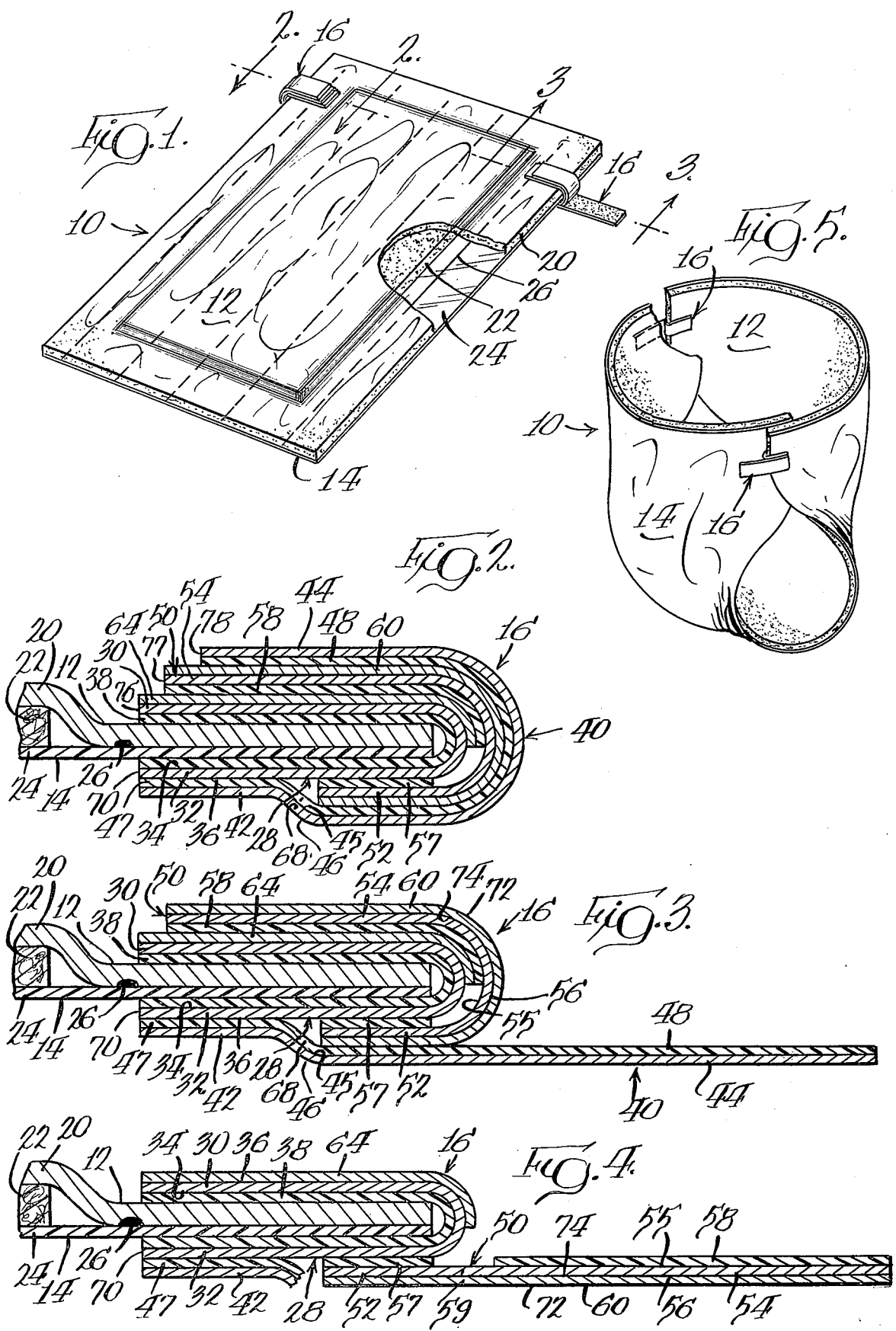

DIAPER HAVING PRIMARY AND SECONDARY TAB FASTENERS

BACKGROUND OF THE INVENTION

This invention relates to disposable diapers. More particularly, this invention relates to disposable diapers adapted to be secured in place by adhesive tabs.

Disposable diapers provide substantial advantages in convenience over diapers intended to be laundered and reused, particularly when they are used away from home. In recent years, many different disposable diapers have been proposed and some have been successful in the marketplace. Typical disposable diaper structures comprise a moisture-retaining layer of high liquid-holding capacity and a moisture-impervious backing sheet therefor, generally made of a plastic film such as polyethylene film or the like. Typical disposable diaper structures are shown in U.S. Pat. No. 3,612,055 to Mesek et al. and in U.S. Pat. No. 26,151 to Duncan et al.

As may be seen from the above-cited patents, it is desirable to obviate the problems that are inherent in closure systems which utilize extraneous fasteners such as safety pins, snaps and zippers. To this end adhesive closure systems have presented acceptable solutions.

In order to protect the adhesive surfaces of the tape tabs, usually a cover strip having a release surface is applied over these adhesive surfaces for subsequent removal when the diaper is about to be used. However, such tabs usually project beyond the confines of the diaper to a considerable extent and interfere with the efficient manufacture and packaging of the diaper.

In an attempt to solve the foregoing problems, U.S. Pat. No. 3,646,937 to Gellert teaches a fastening tab which is provided with a release surface permanently bonded primarily to the inside surface of the diaper. One of the drawbacks of the Gellert arrangement is that in use the adhesive tape fasteners are permanently attached to only one surface of the diaper, generally the outside surface of the backing sheet, and thus the bond between one end of the tape fasteners and the diaper backing sheet is subjected to all of the stresses exerted on the tape fastener during securement or as the infant moves about.

U.S. Pat. No. 3,750,669 to DeLuca shows a fastening tape provided with an adhesive end portion which extends beyond a cover strip for the tape and which is attached to a diaper inner covering or facing. However, such an adhesive end portion, when attached to a fibrous, non-woven facing fabric, may tear the facing fabric upon separation therefrom.

U.S. Pat. No. 3,776,234 to Hoey proposes to fold the tab over on itself at the diaper's edge and to adhesively attach a portion of the folded-over tab segment to an inwardly-folded margin of the diaper backing sheet in order to keep the tab flat against the diaper and thus from interfering with the manufacturing machinery and with the subsequent folding and packaging operations. This requires that the edge of the diaper backing sheet be folded over to present an attachment surface at the front or inside face of the diaper, and a relatively involved tab design is necessary for this purpose. Also, undersirable tearing of the diaper facing fabric may result if such a tab is inadvertently adhesively attached to the facing fabric of the diaper during manufacture.

U.S. Pat. No. 3,616,114 to Hamaguchi et al. discloses an adhesive sealing tape which can be used for releasably interconnecting parts of a diaper or other container. The fixed end of a main tape portion is attached to one side of a first container part. A reinforcing tape portion is provided with a turned up end which is attached to the undersurface of the midregion of the main tape portion, and a part of the reinforcing tape portion is attached to the opposite side of the first container part. The free end of the main tape portion is adapted for attachment to a second container part which is to be secured to the first container part. Thus, the Hamaguchi et al. patent requires two specially interconnected tape portions. Moreover, the turned up end of the reinforcing tape portion causes the folded configuration of the sealing tape to be somewhat bulky.

The adhesive fastener disclosed in U.S. Pat. No. 3,833,456 to Reed et al. can also be attached to both the front and back surfaces of a diaper to provide for force distribution over both surfaces. This particular fastener comprises two coextensive webs with each web having an adhesive coating extending along substantially all of one face. The lower or base web also has a release coating on one end portion of its opposite face so that a portion of the adhesive coating on the upper web is releasably secured thereto while the rest of the adhesive coating on the upper web bonds the two webs together.

A similar tape fastener is shown in U.S. Pat. No. 3,848,594 to Buell wherein the tape fastener is also attached to both the front and back surfaces of the diaper while having a securing portion attached to an adjacent section of the diaper, but has the disadvantage in that each tape fastener is comprised of two or more separate tape segments which are joined together so as to produce a common area of joinder for both fastener anchoring legs and the fastener securing portion and thereby adding complexities and expense to the manufacturing process, as well as requiring careful positioning during diaper manufacture.

SUMMARY OF THE INVENTION

Tape tabs are used on each side of the diaper to secure the diaper about an infant. The diaper includes a backing sheet defining a diaper outside surface and a facing sheet defining a diaper inside surface. Each tab includes a backing web folded over about the longitudinal edge of the diaper and having a pair of anchoring legs receiving a marginal portion of the diaper therebetween. The anchoring legs are permanently attached to the facing and backing sheets.

According to the present invention, a first tape segment has a fixed end permanently attached to a first portion of one anchoring leg, and an adhesive-coated first free end. A second tape segment has a fixed end permanently attached to a second portion of the one anchoring leg, between the first portion and the other anchoring leg, and also has an adhesive-coated second free end. The adhesive-coated first free end is releasably attached to first release means carried on the second free end, and the adhesive-coated second free end is releasably attached to second release means carried on the other anchoring leg.

The first free end is separable from the first release means for securing the diaper about the infant. When it is desired to remove the diaper from the infant for repositioning the diaper or to inspect for wetting, the first tape segment can be severed, and the second tape segment can be separated from the second release means and employed to refasten the diaper about the infant.

The tape tab fasteners of the present invention remain flat against the diaper when in the folded configuration and will not interfere with the diaper manufacturing machinery and the subsequent folding and packaging operations. Additional features of this invention include the utilization of a tape tab which can be pre-assembled and is relatively easy to affix to the diaper, and which provides good bond strength and permanent attachment of the tab to both the diaper facing sheet and backing sheet. Some of the stress imposed on the tab is distributed between the facing sheet and the backing sheet to reduce the possibility of undesirable rupture of the backing sheet.

BRIEF DESCRIPTION OF THE DRAWING

FIG. 1 is a perspective view, partially broken away to show interior detail, of an open unfolded diaper in accordance with the invention;

FIG. 2 is an enlarged fragmentary cross-sectional view of the diaper of FIG. 1 taken along plane 2—2 in which the first and second tape segments are folded over in the storage position;

FIG. 3 is an enlarged fragmentary cross-sectional view of the diaper of FIG. 1 taken along plane 3—3 in which the first tape segment is extended and the second tape segment is folded over in the storage position;

FIG. 4 is a fragmentary cross-sectional view in which the free end of the first tape segment has been severed from the tab and the second tape segment is extended; and FIG. 5 is a perspective view of the diaper of FIG. 1 in a configuration assumed by the diaper when placed about an infant.

DESCRIPTION OF THE PREFERRED EMBODIMENTS

Disposable diaper 10, illustrated in FIGS. 1 and 5, is of substantially quadrilateral configuration and presents inside surface 12 for direction toward an infant and outside surface 14 for direction away from the infant. Adhesive tab fastener means such as tab 16 are attached to diaper 10 for securing diaper 10 about an infant. As described in greater detail below, tab 16 is movable from a folded-over storage position illustrated in FIG. 2 to a working position which is illustrated in FIG. 3.

Referring to FIGS. 1–3, diaper 10 comprises moisture-pervious facing sheet 20, defining diaper inside surface 12 and overlying moisture-retaining absorbent pad 22, and backing sheet 24 which is made of a moisture-impervious material and defines diaper outside surface 14. Absorbent pad 22 is somewhat smaller than the backing sheet 24 and is centrally disposed thereon; however, absorbent pad 22 can be made coextensive with backing sheet 24, if desired. Facing sheet 20 is substantially coextensive with backing sheet 24. Both the facing sheet 20 and pad 22 can be anchored to the backing sheet 24 by means of adhesive beads 26, glue spots or in any other convenient manner. For example, if backing sheet 24 is made of a thermoplastic material, facing sheet 20 and pad 22 can be attached thereto by heat bonding.

As illustrated in FIGS. 2 and 3, adhesive tab 16 comprises a backing web 28 which is folded over about the marginal edge of diaper 10 so as to define first and second anchoring legs 30, 32 each having an inner face 34 and an outer face 36. Anchoring legs 30, 32 preferably are about equal in width and length, and are in a substantially juxtaposed relationship to one another. Anchoring legs 30, 32 receive a marginal portion of the diaper therebetween, and are provided with an adhesive coating which may comprise a continuous adhesive coating 38 on the inner face 34 thereof. First anchoring leg 30 is permanently attached to facing sheet 20 and second anchoring leg 32 is permanently attached to backing sheet 24 by means of adhesive coating 38 which can be a pressure-sensitive adhesive composition, a heat-activated or solvent-activated adhesive composition, or the like.

Tab 16 also includes a first tape segment 40 having a first fixed end 42 and a first free end 44, each having an inner face 45 and an outer face 46. First fixed end 42 is provided with adhesive coating 47 on inner face 45 thereof by means of which first fixed end 42 is permanently attached to second anchoring leg 32, and first free end 44 is provided with pressure-sensitive adhesive coating 48 on inner face 45 thereof. If desired, adhesive coating 47 on first fixed end 42 may be a pressure-sensitive adhesive composition and adhesive coatings 47, 48 on first fixed end 42 and first free end 44, respectively, may comprise a continuous adhesive coating on inner face 45 on first tape segment 40.

As depicted in FIGS. 2–4, tab 16 further includes a second tape segment 50 having a second fixed end 52 and a second free end 54, each having an inner face 55 and an outer face 56. Second tape segment 50 is zone coated with an adhesive to provide a non-tacky region between adhesive coatings 57 and 58 which region can be traversed by an optional line of weakening 59 for facilitating the removal of a soiled diaper from the infant. Second fixed end 52 is provided with adhesive coating 57 on inner face 55 thereof by means of which second fixed end 52 is permanently attached to second anchoring leg 32, and second free end 54 is provided with pressure-sensitive adhesive coating 58 on inner face 55 thereof.

First release means 60 is carried on outer face 56 of second free end 54 for releasable attachment to adhesive coating 48 on first free end 44. First release means 60 provides a first release region which is substantially coextensive with adhesive coating 48 and preferably extends along the outer face 56 of the entire second taped segment 50. First free end 44 is movable from the folded-over storage position illustrated in FIG. 2 wherein first free end 44 is releasably adhered to the first release region, to an extended working position as shown in FIG. 3 wherein the adhesive-coated free end 44 is separated from the first release region and is available for use in securing diaper 10 about an infant. Adhesive coating 48 on first free end 44 faces in the same direction as diaper inside surface 12 when first free end 44 is extended to the working position.

Second release means 64 is carried on outer face 36 of first anchoring leg 30 for releasable attachment to adhesive coating 58 on second free end 54. Second tape segment 50 and second release means 64 provide means for refastening diaper 10 about an infant after the diaper has been placed on the infant. Diaper 10 is initially fastened about an infant by means of first tape segment 40. When it is desired to remove the diaper from the infant, such as for repositioning or to check for wetting, first tape segment 40 can be severed between first fixed end 42 and first free end 44. Diaper 10 can thereafter be refastened about the infant by moving second free end 54 from the folded-over storage position of FIG. 3, in which second free end 54 is releasably adhered to second release means 64, to an extended working position shown in FIG. 4 in which the adhesive-coated second free end 54 is separated from the second release means 64 and is available for use in securing diaper 10 about an infant. Thus, by severing first tape segment 40, diaper 10 can be completely removed from the infant and thereafter refastened on the infant by utilizing the second tape segment 50. The adhesive coating 58 on second free end 54 faces in the same direction as diaper inside surface 12 when second free end 54 is extended to the working position.

To facilitate in severing first tape segment 40, a line of weakening 68 may be provided substantially transversely across first tape segment 40 and between first fixed end 42 and first free end 44.

First fixed end 42 is attached to a first portion of outer face 36 of second anchoring leg 32 adjacent to end 70, and second fixed end 52 is attached to a second portion of second anchoring leg 32 between the first portion and first anchoring leg 30. Both tape segments 40, 50 are thereby permanently attached to backing web 28 and the backing web is directly attached to both facing sheet 20 and backing sheet 24. This arrangement has the feature of distributing some of the stresses imposed on tape segments 40, 50 to both facing sheet 20 and backing sheet 24, especially if backing sheet 24 is extensible or begins to stretch due to overloading.

As depicted in FIGS. 2–4, second tape segment 50 is zone coated with an adhesive such that adhesive coating 57 on second fixed end 52 is spaced from adhesive coating 58 on second free end 54. It is therefore desirable for second release means 64 to be correspondingly spaced from adhesive coating 57 on second fixed end 52. The uncoated portion of tape segment 50 between adhesive coatings 57, 58 facilitates tearing or severing of tape segment 50 for removal of the diaper from the infant, and also provides more elasticity in the region between adhesive coatings 57, 58 to dissipate stress which is imposed on the tape segment as the infant moves about, thereby minimizing the load on second free end 54. If desired, first tape segment 40 can also be zone coated with an adhesive such that adhesive coatings 47, 48 are spaced apart.

Tab 16 includes backing web 28, first tape segment 40 and second tape segment 50 and has the feature that it can be manufactured as a separate sub-assembly which can easily be secured to the marginal edge of the diaper.

Release means such as first release means 60 in FIGS. 2–4 may comprise a ribbon segment or release strip carried by second tape segment 50 and provided with a release coated face 72 which provides the release region, and an adhesive coating on opposite face 74 by means of which the release strip is anchored to second tape segment 50. Release coated face 72 faces generally in the same direction as diaper inside surface 12 and is substantially coextensive with adhesive coating 48 on first free end 44 when first tape segment 40 is folded to the storage position. Alternatively, release means 60 may comprise a release coating, such as a silicone release compound, or the like, on the outer face 56 of second tape segment 50 and which is substantially coextensive with adhesive coating 48 on first free end 44 when first tape segment 40 is folded to the storage position.

It is desirable to provide a gripping means to facilitate grasping tape segments 40, 50 to separate adhesive-coated free ends 44, 54 from release means 60, 64 preparatory to fastening the diaper about an infant. As shown in FIG. 2, terminal edge 76 of first anchoring leg 30, terminal edge 77 of second free end 54, and terminal edge 78 of first free end 44 may terminate in a step-like configuration. Release means 60, 64 extend to edges 76, 77 so that first release means 60 extends beyond the edge 78 of adhesive-coated first free end 44 and second release means 64 extends beyond the edge 77 of adhesive-coated second free end 54 when the tape segments are in the storage position. This configuration enables a user to conveniently grip first free end 44 to separate first free end 44 from first release means 60 without simultaneously peeling the second free end 54 from its releasable engagement with second release means 64. Similarly, second free end 54 can be easily gripped and separated from second release means 64 when desired.

Adhesive tabs suitable for the purposes of the present invention can be made from a wide variety of materials, provided that such materials are sufficiently flexible. Preferred materials for this purpose are polyalkylene webs such as polyethylene sheet, polypropylene sheet, and the like. Particularly preferred are webs which are oriented along the narrow dimension of the tab or webs which have filament reinforcements therein.

The pressure-sensitive adhesive layers such as adhesive coatings 48, 58 are provided by applying a coating of a pressure-sensitive adhesive composition known in the art to the appropriate surface of tape segments 40, 50. The applied adhesive shall have good tack, good cohesive strength, good resistance to moisture and good resistance to aging. Illustrative of such adhesive compositions are mixtures of natural or synthetic rubber, zinc oxide, and various resins, also latices of natural or synthetic rubber, or water dispersions of acrylic tacky polymers or copolymers, and the like.

Anchored release strips can be made from smooth plastic film having a relatively non-adhering surface, from paper coated with a silicone release compound, or from similar release materials. A number of appropriate release coatings may be used with the present invention. Examples of such coatings are disclosed in U.S. Pat. No. 2,822,290 to Webber; U.S. Pat. No. 2,800,862 to Sermattei; and U.S. Pat. No. 2,985,554 to Dickard.

Several different types of facing materials may be used for diaper facing sheet 20. For example, facing sheet 20 may be made up of a mixture of fibers consisting predominantly of inexpensive short cellulosic fibers such as wood pulp fibers or cotton linters, in amounts of about 75% to about 95%, the balance being textile length fibers such as rayon as described in U.S. Pat. No. 3,663,348 to Liloia et al.

Facing sheet materials suitable for use in this invention can have fabric weights in the range of about 1 to 5 oz./yd.$^2$ and densities of less than 0.15 g./cc., generally in the range between 0.05 and 0.1 g./cc. The dry strength of the facing sheet for a fabric having a weight of about 1.5 oz./yd.$^2$ is at least 0.15 lbs./in. of width in the machine direction and at least 0.1 lbs./in. of width in the cross direction. Such fabrics have unusually good elongation, loft, softness, and drape characteristics in comparison to prior products incorporating any substantial amount of short fibers.

Facing sheet 20 may also be made of an apertured, non-woven fabric which is formed, for example, in accordance with the teachings of commonly assigned U.S. Pat. Nos. 2,862,251, 3,081,514 and 3,081,515.

Briefly, such fabrics are foraminous structures wherein groups or groupings of fibers have been rearranged from a fibrous non-woven starting web into positions surrounding less dense fabric portions by passage of a fluid through the starting material. The fibers within the groupings are mechanically interlocked, and may be arranged into various patterns, as is well known by those skilled in the art. A suitable binder may be utilized to help retain the fibers in their rearranged locations, as is well known by those skilled in the art. The fabric can be made of naturally occurring fibers, synthetic fibers, or blends thereof. Typical facing sheets made of a polyester type material can have a weight of about 0.75 oz./yd.$^2$.

In addition, facing sheet 20 can be formed of a non-apertured material, such as a non-woven isotropic web, of the like. In all of the aforementioned facing materials, the material should be relatively hydrophobic so as to retard wicking within the facing layer. Also suitable are porous polymeric sheet materials such as polyalkylene webs having a fibrous surface, and the like.

Highly moisture-absorbent pad or batt 22, which usually is substantially rectangular in shape but smaller than the facing sheet and the backing sheet, can be formed in accordance with the teachings of U.S. Pat. No. 3,612,055 to Mesek et al. If desired, a highly moisture-absorbent layer can be provided substantially coextensive with backing sheet 24 and facing sheet 20.

A suitable backing sheet material for the diapers embodying the present invention can be an opaque polyethylene web about 0.001 inch thick. Another suitable material for this purpose is a polyethylene terephthalate web having a thickness of about 0.0005 inch. Typical disposable diapers which can be fitted with tab-type adhesive fasteners described hereinabove are shown in U.S. Pat. No. 3,612,055 to Mesek et al. and in U.S. Pat. No. 3,683,916 to Mesek et al. Other suitable disposable diaper structures which can be improved by the present tab-type fasteners are shown in U.S. Pat. No. 26,151 to Duncan et al.

In use, a diaper equipped with the adhesive fasteners of the present invention is applied to the infant by laying out the diaper on a suitable flat surface and placing the infant thereof so that the waist-underlying end of the diaper is that having the tab fastener means. The other end of the diaper then extends downwardly between the infant's legs. Next, the downwardly extending end of the diaper is brought up between the infant's legs to a position contiguous with the front of the infant's waist. The diaper is thereafter secured to the infant by placing the corners of the waist portion of the abdomen-covering end as far around the infant's waist as they will go and by bringing the corners of the underlying end of the diaper into an overlapping relationship with the aforementioned corners so that the diaper snugly encircles the infant's waist and provides a custom fit. The adhesive fasteners are then prepared for use by pulling first free end 44 away from its temporary engagement with first release means 60, exposing adhesive coating 48 which was releasably adhered to first release means 60 and separable therefrom. First tape segments 40 are then used to secure the diaper in the desired position by simply urging the pressure-sensitive adhesive surfaces in contact with the adjacent outer surface of the diaper. The applied diaper assumes the configuration illustrated in FIG. 5. When it is desired to remove the diaper from the infant for repositioning or to inspect for wetting, first tape segment 40 can be severed and second tape segment 50 can be employed to refasten the diaper about the infant, as described hereinabove.

The foregoing description and the drawing are illustrative but are not to be taken as limiting. Still other variations and modifications are possible without departing from the spirit and scope of the present invention.

We claim:
1. A disposable diaper having a facing sheet defining a diaper inside surface for direction toward an infant, a moisture-impervious backing sheet substantially coextensive with said facing sheet and defining a diaper outside surface, an absorbent panel positioned between said facing sheet and said backing sheet, and an adhesive tab fastener means which comprises:
   a backing web folded over to form first and second anchoring legs each having an inner face and an outer face and receiving a marginal portion of the diaper between said anchoring legs, said inner face of said anchoring legs being provided with an adhesive coating by means of which said anchoring legs are permanently attached to said diaper marginal portion;
   a first tape segment having a first fixed end and a first free end, each having an inner face and an outer face, said first fixed end being permanently attached to said second anchoring leg and said first free end being provided with a pressure-sensitive adhesive coating on said inner face thereof;
   a second tape segment having a second fixed end and a second free end, each having an inner face and an outer face, said second fixed end being permanently attached to said second leg and said second free end being provided with a pressure-sensitive adhesive coating on said inner face thereof;
   first release means carried on said outer face of said second free end for releasable attachment to said adhesive coating on the first free end;
   second release means carried on said outer face of said first anchoring leg for releasable attachment to said adhesive coating on the second free end;
   said first free end of said first tape segment being separable from said first release means to make said first free end available for securing said diaper about an infant;
   whereby said diaper can be refastened about an infant by severing said first tape segment between said first fixed end and said first free end, and thereafter moving said second free end of said second tape segment from a folded-over storage position in which said second free end is releasably adhered to said second release means to a working position in which said second free end is available for securing said diaper about said infant.
2. Th disposable diaper as defined in claim 1 wherein said first fixed end is attached to a first portion of said second leg adjacent the edge of said second leg, and wherein said second fixed end is attached to a second portion of said second leg and between said first portion and said first leg.
3. The disposable diaper as defined in claim 1 wherein an adhesive coating is provided on said inner face of said second fixed end by means of which said second fixed end is attached to said second leg, said adhesive coating on said second free end being spaced from said adhesive coating on said second fixed end, and said second release means being correspondingly spaced from said adhesive coating on said second fixed end.

4. The disposable diaper as defined in claim 3 wherein a transverse line of weakening is provided in said second tape segment between said adhesive coatings thereon.

5. The disposable diaper as defined in claim 1 wherein a line of weakening is provided substantially transversely across said first tape segment and between said first fixed end and first free end thereof to facilitate in severing said first tape segment.

6. The disposable diaper as defined in claim 1 wherein said adhesive coating on said inner face of said anchoring legs comprises a continuous adhesive coating on one face of said backing web.

7. The disposable diaper as defined in claim 1 wherein a pressure-sensitive adhesive coating is provided on said inner face of said first fixed end by means of which said first fixed end is attached to said second leg, said adhesive coatings on said first fixed end and said first free end comprising a continuous adhesive coating on one face of said first tape segment.

8. The disposable diaper as defined in claim 1 wherein said first release means is carried on said outer face of said second end and provides a release region substantially coextensive with said pressure-sensitive adhesive coating on said first free end;
said first free end being movable from a folded-over storage position wherein said first free end is releasably adhered to said first release region to a working position wherein said adhesive-coated first free end of said first tape segment is available for use in securing said diaper about an infant.

9. The disposable diaper as defined in claim 8 wherein said adhesive coating on said first free end faces in the same direction as said diaper inside surface when said first tape segment is extended to said working position.

10. The disposable diaper as defined in claim 1 wherein said adhesive coating on said second free end faces in the same direction as said diaper inside surface when said second tape segment is extended to said working position.

11. The disposable diaper as defined in claim 8 wherein said first release means is a release coating on said outer face of said second free end, and said second release means is a release coating on said outer face of said first anchoring leg.

12. The disposable diaper as defined in claim 11 wherein each said coating comprises a silicone release compound.

13. The disposable diaper as defined in claim 8 wherein said first release means extends beyond the terminal edge of said adhesive coating on said first free end when said first tape segment is in said storage position to facilitate in separating said first tape segment from said first release means when securing said diaper about the infant, and
wherein said second release means extends beyond the terminal edge of said adhesive coating on said second free end when said second tape segment is in said storage position to facilitate in separating said second tape segment from said second release means when refastening said diaper about the infant.

14. The disposable diaper as defined in claim 1 wherein said first release means extends along the outer face of the entire second tape segment, and wherein said adhesive coatings on said first free end and said first fixed end comprise a continuous adhesive coating on the inner face of said first tape segment.

* * * * *